United States Patent
Heismann

(10) Patent No.: US 6,997,610 B2
(45) Date of Patent: Feb. 14, 2006

(54) CALIBRATION OF THE TRANSFORMATION OF SPECTRAL X-RAY ATTENUATION VALUES IN DENSITY AND ATOMIC NUMBER INFORMATION

(75) Inventor: Bjoern Heismann, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 100 days.

(21) Appl. No.: 10/772,241

(22) Filed: Feb. 6, 2004

(65) Prior Publication Data

US 2004/0218728 A1 Nov. 4, 2004

(30) Foreign Application Priority Data

Feb. 7, 2003 (DE) .................................... 103 05 105

(51) Int. Cl.
*G01D 18/00* (2006.01)

(52) U.S. Cl. .................... 378/207; 378/18; 378/901; 250/252.1

(58) Field of Classification Search ............... 378/207, 378/62, 18, 4, 19, 95, 56, 45, 901, 98.9, 98.11; 250/252.1

See application file for complete search history.

(56) References Cited

U.S. PATENT DOCUMENTS

| | | | |
|---|---|---|---|
| 4,962,514 A | | 10/1990 | Hart et al. .................... 378/18 |
| 4,985,906 A | | 1/1991 | Arnold ........................ 378/18 |
| 6,362,471 B1 | * | 3/2002 | Spitz et al. .............. 250/252.1 |
| 6,490,336 B1 | * | 12/2002 | Suess et al. .................. 378/18 |
| 6,570,955 B1 | * | 5/2003 | Siffert et al. ................. 378/54 |
| 6,574,302 B1 | * | 6/2003 | Adriaansz .................... 378/54 |

FOREIGN PATENT DOCUMENTS

DE 10143131 4/2003

* cited by examiner

*Primary Examiner*—Edward J. Glick
*Assistant Examiner*—Irakli Kiknadze
(74) *Attorney, Agent, or Firm*—Harness, Dickey & Pierce, P.L.C.

(57) ABSTRACT

A method is for calibration of a transformation of at least two X-ray attenuation values (which are determined using different X-ray spectra) for a material, to a value for the density and a value for the atomic number of the material. A first distribution is recorded of first X-ray attenuation values obtained from a calibration phantom using a first X-ray spectrum, and a second distribution is recorded of second X-ray attenuation values obtained from the calibration phantom using a second X-ray spectrum. The recorded X-ray attenuation values are used to produce a density function and to produce an atomic number function. A value for the density and for the atomic number of the calibration sample is determined with the aid of the density function and the atomic number function, and a discrepancy between the determined values and the actual density and atomic number of the calibration sample is found. The discrepancy is used for producing a mapping rule which changes the values determined by the density function and the atomic number function to the actual values.

10 Claims, 2 Drawing Sheets

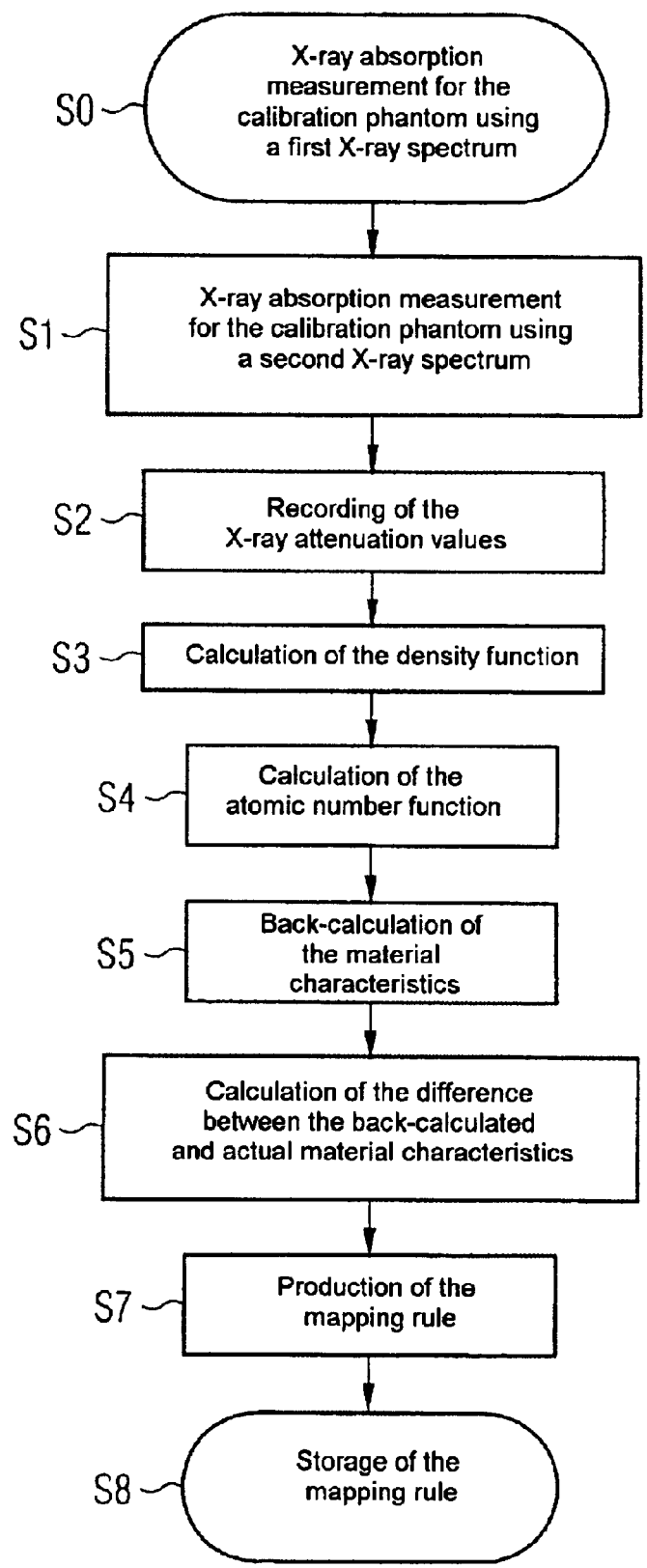

CALIBRATION OF THE TRANSFORMATION OF SPECTRAL X-RAY ATTENUATION VALUES IN DENSITY AND ATOMIC NUMBER INFORMATION

The present application hereby claims priority under 35 U.S.C. §119 on German patent application number DE 103 05 105.8 filed Feb. 7, 2003, the entire contents of which are hereby incorporated herein by reference.

FIELD OF THE INVENTION

The present invention generally relates to the calibration of X-ray systems; preferably which are designed to separately determine the distribution of the density and effective atomic number in an object that is being examined.

BACKGROUND OF THE INVENTION

The classical radiographic methods, such as computer tomography, mammography, angiography, X-ray inspection techniques or comparable methods produce a display of the attenuation of an X-ray beam along its path from the X-ray source to the X-ray detector. The attenuation is caused by the medium or materials that the radiation passes through along the beam path. It is normally indicated or recorded in the form of the attenuation coefficient $\mu$, which is defined as the logarithm of the ratio of the intensity of the attenuated radiation to the primary radiation with respect to a path normal.

Increased attenuation values may be caused either by materials having a relatively high atomic number, such as calcium in the skeleton or iodine in a contrast agent, or by a higher material density, for example in the case of a lung node. The local attenuation coefficient $\mu$ at a measurement point is dependent on the X-ray energy injected into the tissue or material located there, on the local tissue or material density $\rho$, and on the atomic number Z of the material at the measurement point.

The energy-dependent X-ray absorption of a material, as is defined by its effective atomic number, is thus superimposed on the X-ray absorption that is influenced by the material density. Materials and tissues of different chemical or physical composition may thus have identical attenuation values in the X-ray image. Conversely, on the other hand, it is impossible to deduce the material composition of an object being examined from the attenuation value in an X-ray recording.

Correct interpretation of the distribution (which is thus actually rather unclear) of the X-ray attenuation values in an X-ray image produced using a radiographic examination method can generally be carried out only on the basis of morphological criteria in the medical sector, and generally requires a radiologist with decades of experience in his field. Nevertheless, in some circumstances, structures which occur with increased attenuation values in the imaging process for an X-ray examination cannot be clearly classified. For example, it is difficult to distinguish between calcification close to the hilus on a thorax overview recording and a vessel which is located orthogonally with respect to the imaging plane. It is also virtually impossible to distinguish, for example, between diffuse calcification and fresh bleeding.

Even in the case of material and safety examinations, the examiner generally supplements the information in the display of an attenuation value distribution by his personal specialist knowledge and professional experience. Nevertheless, it is impossible, for example, for him to distinguish reliably between plastic-bonded explosive mixtures and a non-explosive plastic directly from an X-ray image.

Methods for displaying material-characteristic values are required for this purpose. One such method is described, for example, in the German Patent Application with the file reference 10143131.7. The method makes use of the fact that, with a defined X-ray spectrum, the X-ray attenuation values for specific value pairs ($\rho$, Z), namely combinations of the material density $\rho$ and of the atomic number Z, are identical and together form a so-called iso-absorption line in the $\rho$-Z plane. If a second, different type of X-ray spectrum is used, a second iso-absorption line with a different profile is obtained, which intersects the first at a point whose coordinates in the $\rho$-Z plane reflect the material density $\rho$ and the atomic number Z of the material through which the beam has passed.

In the context of this description, the expression atomic number is not used in the strict sense relating to the elements. Instead, this denotes an effective atom number of a tissue, or material, which is calculated from the chemical atomic numbers and atomic weights of the elements which are involved in the formation of the tissue or material. The precise equation for determination of an atomic number in the sense described above is quoted in the patent application that has been mentioned.

Furthermore, the expression X-ray spectrum in this context is not restricted to the spectral distribution of X-ray radiation emitted from an X-ray source, but additionally takes into account the different weighting of different spectral areas in the emission spectrum of the X-ray tube at the X-ray detector end. A measured attenuation value is thus obtained from the direct attenuation of the beam spectrum emitted from the X-ray tube and the spectrum efficiency of the X-ray detector is used. Both values are system-specific variables and may vary over the course of time.

The profile of an iso-absorption line in the $\rho$-Z plane is critically influenced by the respective spectral distribution of an X-ray spectrum. Since the recording of the spectral profile of the X-ray spectrum in an X-ray system by measurement is highly complex, the attenuation values of various calibration materials are determined in an X-ray system with the various X-ray spectra that are used in it in order to avoid the need for corresponding measurements. The measurements are repeated at specific intervals in order to take account of any changes in the X-ray spectra with time. The calibration materials differ from one another in their material densities and, preferably, in their atomic number as well. The measured values form support points for subsequent calculation of iso-absorption lines. The iso-absorption lines are used to calculate a density function $\rho(\mu_1, \mu_2)$ and an atomic number function $Z(\mu_1, \mu_2)$, which associate a density and an atomic number respectively, with a value pair of attenuation values $\mu_1$ and $\mu_2$ for a material when using a first and a second X-ray spectrum.

However, in practice, it has been found that the calculation of the density and atomic number functions is highly inaccurate. Acceptable results are achieved only with calibration samples with medium-range atomic numbers. Density and atomic number functions obtained from corresponding calibration measurements are thus highly unreliable in the area both of small and large atomic numbers.

However, if calibration samples with widely differing atomic numbers are used, then the measured X-ray attenuation values are subject to major errors. Further, the family of iso-absorption line curves that is determined does not allow exact definition of the density and atomic number functions for an X-ray apparatus.

In practice, this results in the difficulty that the density and atomic number functions calculated in the described manner do not reproduce the exact values of the density and atomic number of the calibration samples used to produce them. These discrepancies between the calculated and "measured values" and the actual and "nominal values" are also non-linearly dependent on the attenuation values $\mu_1$ and $\mu_2$, and cannot be handled by analytic methods. In many cases, this means that reliable characterization of a material or tissue is impossible.

SUMMARY OF THE INVENTION

One object of an embodiment of the present invention is therefore to specify a method for reliable calibration of the transformation of X-ray attenuation values (which are determined using different X-ray spectra) for a material to a value for the density and a value for the atomic number of the material, which method in particular does not have the disadvantages mentioned above.

The method, in one embodiment, may be implemented in a form which can be carried out automatically in a computer program product and/or in computer program (which may be implemented via a computer readable medium and/or which may be embodied as a computer signal).

The solution, in one embodiment, includes a method for calibration of a transformation of at least two X-ray attenuation values (which are determined using different X-ray spectra) for a material to a value for the density and a value for the atomic number of the material. In a first method step, a first distribution is recorded of first X-ray attenuation values which are obtained from a calibration phantom using a first X-ray spectrum, and a second distribution of second X-ray attenuation values which are obtained from the calibration phantom using a second X-ray spectrum. The calibration phantom has at least three calibration samples which are arranged physically separately from one another and have different densities and/or atom numbers.

The recorded X-ray attenuation values are used to produce a density function which associates a value for a density of the material with the combination of a first recorded X-ray attenuation value for a material with a second recorded X-ray attenuation value for the material, and to produce an atomic number function, which associates a value for an atomic number of the material with a combination of the first recorded X-ray attenuation value for the material with the second recorded X-ray attenuation value for the material. A value for the density and for the atomic number of the calibration sample is determined from the measured X-ray attenuation values with the aid of the density function and the atomic number function from the first and second X-ray attenuation values recorded for a calibration sample, and the discrepancy between the determined values and the actual density and atomic number of the calibration sample is found. The discrepancy which is found may be used as the basis for producing a mapping rule which changes the values determined by the density function and the atomic number function to the actual values.

The above object may also be achieved by a computer program product for calibration of a transformation of at least two X-ray attenuation values (which are determined using different X-ray spectra) for a material to a value for the density and a value for the atomic number of the material, having program instructions for production of a density function and of an atomic number function from the X-ray attenuation values recorded from a calibration phantom using at least three calibration samples which are arranged physically separately from one another and have different densities and/or atomic numbers.

Furthermore, the computer program product may contain program instructions for calculation of the values for the density and atomic number of a calibration sample with the aid of the density function and of the atomic number function from the first and second X-ray attenuation values recorded for the calibration sample. It may further contain program instructions for calculation of the discrepancy between the values for the density and atomic number calculated for the calibration sample and the actual density and atomic number of the calibration sample. Finally, it may also contain program instructions for determination of the discrepancy between the values calculated for the density and atomic number of the calibration sample and the actual density and atomic number of the calibration sample. Further program instructions are designed to produce a mapping rule which changes the values determined by the density function and the atomic number function to the actual values based on the discrepancy determined.

The method according to an embodiment of the invention allows the calibration of energy-resolving X-ray absorption measurements such as those used in computer tomography, material testing or safety inspection technology. It allows exact determination of the density and atomic number even of materials and tissues which have a low or a high atomic number.

Further advantages, features and details of the invention will become evident from the exemplary embodiment of the application described in the following text and from the drawings.

BRIEF DESCRIPTION OF THE DRAWINGS

The present invention will become more fully understood from the detailed description of preferred embodiments given hereinbelow and the accompanying drawing, which is given by way of illustration only and thus are not limitative of the present invention, and wherein:

FIG. 4 shows the steps in a method according to the invention, in the form of a flowchart.

DETAILED DESCRIPTION OF THE PREFERRED EMBODIMENTS

Figure 1:
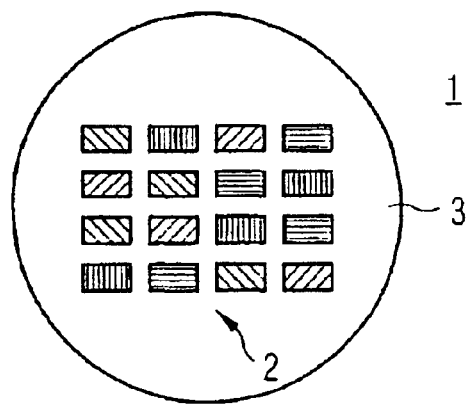
FIG. 1 shows a calibration phantom with calibration samples for calibration of the transformation matrix.

FIG. 1 shows a calibration phantom 1 for use in the calibration measurement according to an embodiment of the invention. This includes two or more calibration samples 2, which are arranged in a mount material 3. The number of calibration samples 2 should not be less than 3. The calibration samples 2 preferably differ from one another both in their density and in their atomic number. However, it is sufficient for two calibration samples to in each case differ in one of the two parameters.

The size of the calibration samples must be chosen on the basis of the task of the respective X-ray apparatus to be calibrated. For medical, computer-tomographic examinations, a suitable size for the calibration samples is in the range from millimeters to centimeters. For industrial computer-tomographic or other radiographic examination methods, it may also be suitable to use calibration samples with a size in the decimeter range.

Solids are preferably used as material for the calibration samples, since they can be arranged particularly easily in a calibration phantom. However, if liquid calibration materials are required, then the liquids are introduced into a container which is or can be closed, and are arranged in this encapsulated form in the calibration phantom 1. By way of example, metals such as lithium, aluminum, sodium, potassium and their compounds, for example salts or the like, are suitable for use as calibration materials 2. Plastics or organic compounds, for example compounds similar to the body with varying proportions of hydrogen, oxygen, carbon, nitrogen and calcium may likewise be used. The use of a water sample is particularly worthwhile in the medical field. Stabilizing material, preferably of plastic such as polymethylmethacrylate, is expediently used as mount material for the calibration phantom.

Figure 2:
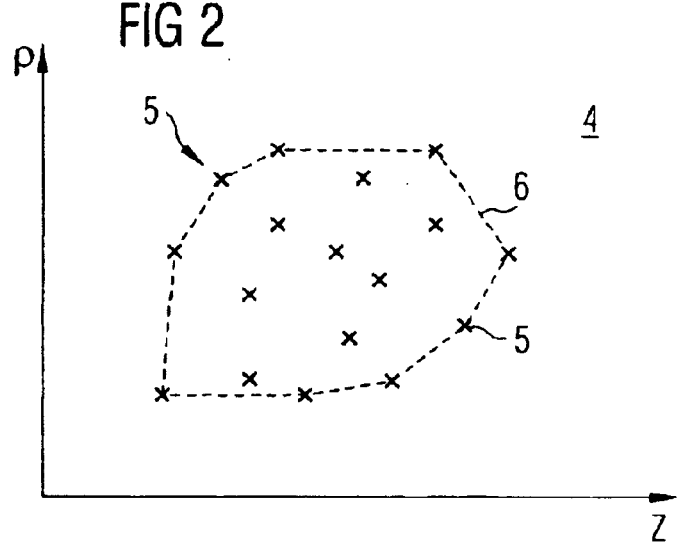
FIG. 2 shows the support points, obtained from a measurement of the calibration samples shown in FIG. 1, in the ρ-Z plane.

The choice of materials is governed primarily by the examinations to be carried out on the corresponding X-ray system. The density and atomic number of each calibration material are associated, as is illustrated in FIG. 2, with a coordinate 5 in the ρ-Z plane 4. The coordinates 5 of all the calibration samples are distributed over an area which can be bounded by a closed polygon 6. This polygon 6 connects the outer coordinate points 5 in the ρ-Z plane 4 such that each of these points is located either at a corner of the polygon 6 or within it. The density/atomic number combinations of the tissues or materials to be examined on the X-ray system to be calibrated should lie within the polygon 6 defined by the choice of the calibration samples, or should at least be located close to the polygon 6. At the very least, the calibration samples should be chosen such that the density and atomic number values of the tissues and materials which are of interest for examination fall in the area covered by the polygon 6, or in its immediate vicinity.

It has been found expedient to use calibration samples whose density and atomic number values lie close to one another in the areas which are of particular interest for examination. This results in a dense network of support points 5 in the ρ-Z plane 4, thus making it possible to achieve greater accuracy for the calculation of the density and atomic number functions.

Figure 3:
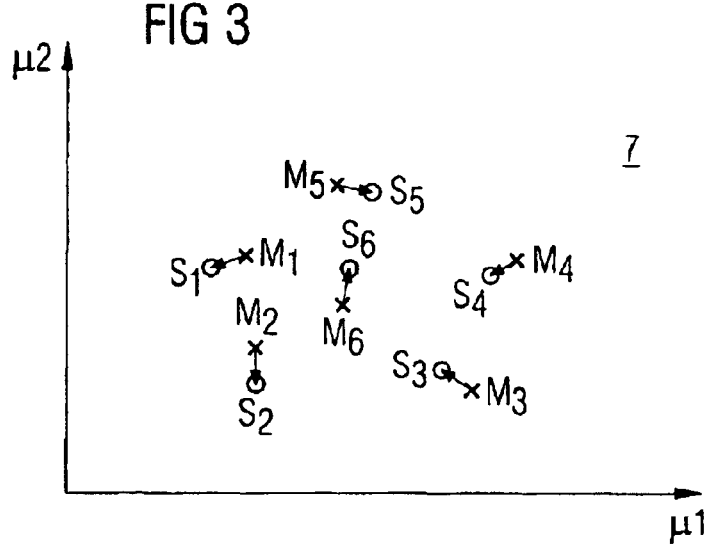
FIG. 3 shows the discrepancy between the calibration measured values and the nominal values for the density function $\rho(\mu_1, \mu_2)$.

If the calibration materials are measured using two X-ray spectra that are not the same as one another, then a measurement point $M_x$ (x ⑧ ⑩) is obtained in the attenuation value plane 7 for each calibration sample 2 as illustrated in FIG. 3. Analogously, for calibration measurements with more than two X-ray spectra, a point is obtained in an attenuation value area whose dimension corresponds to the number of X-ray spectra that are not the same as one another.

If the density and atomic number functions previously calculated from these measurement points $M_x$ are applied to these measurement points $M_x$ themselves, then values are typically obtained which differ from the actual density or atomic number, that is to say the material characteristics of the respective calibration sample. The attenuation values which can be associated with the actual material characteristics of a calibration sample 2 corresponding to the determined functions $\rho(\mu_1, \mu_2)$ and $Z(\mu_1, \mu_2)$ differ in the opposite manner from the measurement values $M_x$. These are entered as nominal values $S_x$ in the diagram 7 in FIG. 3. As is illustrated in FIG. 3, the discrepancy between the nominal values ($S_x$ (x ⑧ ⑩) and the measurement values $M_x$ is in this case extremely non-linear.

A calibration method which will be explained in more detail with reference to FIG. 4 is proposed in order to correct for the discrepancy between the material characteristics of the calibration samples as calculated from the measured values and their actual characteristics.

The method starts in step S0 with an X-ray measurement, for example a computer-tomographic measurements of the calibration phantom 1 using first X-ray spectrum. The volumes of the individual calibration samples 2 are measured completely during this process. In step S1, the calibration phantom 1 is measured in the same way as in step S0, but using a second X-ray spectrum, which is not the same as the first. The planar or three-dimensional distributions of the attenuation values of the calibration phantom 1 that are obtained are recorded in the step S2, and/or are stored in the data memory of a data processing device. This data is used in the next step S3 to calculate the density function $\rho(\mu_1, \mu_2)$ and, in the subsequent step S4, to calculate the atomic number function $Z(\mu_1, \mu_2)$.

The associated material characteristics are calculated back from the attenuation values $\mu_1$ and $\mu_2$ for each calibration sample 2 in the step S5, using the functions produced in this way. The difference between the values obtained in this way and the actual material characteristics of the respective calibration samples 2 is calculated in step S6. For this purpose, the density and atomic number of each calibration sample are preferably recorded a priori, for example in a list or file. The differences can be determined separately for the density and for the atomic number of each calibration sample. These differences are used in step S7 to produce a mapping rule, which results in a linear map in the form of a transformation matrix [D] for the density function and [Z] for the atomic number function.

The two transformation matrices may also be produces by choosing their elements such that the absorption values of the nominal values $S_x$ ($S_1$ to $S_7$ in FIG. 3) coincide with the measured values $M_x$ ($M_1$ to $M_7$ in FIG. 3) in the attenuation plane 7 or in an attenuation area.

This results in a calibration of the transformation of two X-ray attenuation values $\mu_{1x}$ and $\mu_{2x}$ (determined using different X-spectra) for material X to a value for the density $\rho_x$ of the material:

$$\rho_x = [D]\rho(\mu_{1x}, \mu_{2x}), \text{ and}$$

for the associated atomic number $Z_x$ of the material:

$$Z_x = [Z]Z(\mu_{1x}, \mu_{2x}) = Z'(\mu_{1x}, \mu_{2x}),$$

where ρ' and Z' represent the calibrated density and atomic number functions, respectively, for the relevant X-ray system.

Since the X-ray spectra in a system vary with time, the described calibration measurement must generally be repeated at regular or irregular intervals. Currently determined mapping matrices therefore cannot generally be applied to older measurements. The mapping rules determined during the calibration processes in the form of matrices [D] and [Z] or the functions ρ' and Z' are therefore preferably stored in a data storage medium in step S8 in FIG. 4, so that they can be used for calibration at any time for evaluation of examinations carried out previously.

The described method steps for calculation of the density and atomic number functions as well as the mapping rules are preferably in the form of instructions in a computer program. The computer program may be stored in a data storage medium and may be run on a data processing system or computer in order to carry out the described method. Further, the computer program may be embodied in a computer signal, such as a carrier signal, sync signal, etc., and may thus be transmitted via a satellite, the Internet, etc.

The program can be offered to the user in the form of a computer-readable storage medium. The storage medium may be a built-in medium installed inside a computer main body or a removable medium arranged so that it can be separated from the computer main body. Examples of the built-in medium include, but are not limited to, rewriteable involatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable involatile memory, such as memory cards; and media with a built-in ROM, such as ROM cassettes.

The proposed calibration method allows reliable calibration of the transformation of attenuation values obtained from a tissue or material using different X-ray spectra to the indication of the density and of the atomic number of the material, with no need to separately record the spectral parameters of the X-ray system. In practice, this results in an accuracy of ±0.1 in the density transformation, and of ±20 mg/cm$^3$ in the atomic number transformation.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for calibration of a transformation of at least two X-ray attenuation values determined using different X-ray spectra for a material to a value for the density and a value for the atomic number of the material, the method comprising:

recording a first distribution of first X-ray attenuation values obtained from a calibration phantom using a first X-ray spectrum, and a second distribution of second X-ray attenuation values obtained from the calibration phantom using a second X-ray spectrum, wherein the calibration phantom includes at least three calibration samples arranged physically separately from one another and including at least one of different densities and atomic numbers;

calculating a density function which associates a value for a density of the material with a combination of a first recorded X-ray attenuation value for a material with a second recorded X-ray attenuation value for the material; and calculating an atomic number function, associating a value for an atomic number of the material with a combination of the first recorded X-ray attenuation value for the material with the second recorded X-ray attenuation value for the material; and determining a value for the density and for the atomic number of the calibration sample with the aid of the density function and the atomic number function from the first and second X-ray attenuation values recorded for a calibration sample;

determining a discrepancy between the determined values and the actual density and atomic number of the calibration sample; and using the discrepancy as the basis to produce a mapping rule which changes the values determined by the density function and the atomic number function to the actual values.

2. The method as claimed in claim 1, wherein calibration samples are used whose values for the density and atomic number cover the area of interest for an X-ray examination.

3. The method as claimed in claim 2, wherein a greater number of calibration samples are used in the density and atomic number areas of interest.

4. The method as claimed in claim 3, wherein the mapping rule is stored in a data processing system.

5. The method as claimed in claim 2, wherein the mapping rule is stored in a data processing system.

6. The method as claimed in claim 1, wherein a greater number of calibration samples are used in the density and atomic number areas of interest.

7. The method as claimed in claim 6, wherein the mapping rule is stored in a data processing system.

8. The method as claimed in claim 1, wherein the mapping rule is stored in a data processing system.

9. A computer readable medium comprising a computer program causing a computer device to perform the method of claim 1.

10. A computer program product for calibration of a transformation of at least two X-ray attenuation values, determined using different X-ray spectra, for a material, the computer program product, when run on a computer, causing the computer to perform the following steps:

producing a density function and an atomic number function from the X-ray attenuation values recorded from a calibration phantom at at least two different X-ray spectra using at least three calibration samples arranged physically separately from one another and including at least one of different densities and different atomic numbers;

calculating values for the density and atomic number of a calibration sample with the aid of the density function and of the atomic number function from the first and second X-ray attenuation values recorded for the calibration sample;

calculating a discrepancy between the values for the density and atomic number calculated for the calibration sample and the actual density and atomic number of the calibration sample; and producing a mapping rule which changes the values determined by the density function and the atomic number function to the actual values based on the discrepancy determined.

* * * * *